(12) United States Patent
Romero

(10) Patent No.: US 11,638,726 B2
(45) Date of Patent: May 2, 2023

(54) METHODS FOR PRODUCING PROBIOTICS FORTIFIED AVIAN EGGS AND EGG PRODUCTS AND FORMULATIONS THEREOF

(71) Applicant: TALL GOODS, LLC, Santa Fe, NM (US)

(72) Inventor: Andrea Romero, Santa Fe, NM (US)

(73) Assignee: TALL GOODS LLC, Santa Fe, NM (US)

( * ) Notice: Subject to any disclaimer, the term of this patent is extended or adjusted under 35 U.S.C. 154(b) by 0 days.

(21) Appl. No.: 17/642,689

(22) PCT Filed: Sep. 25, 2020

(86) PCT No.: PCT/US2020/052855
§ 371 (c)(1),
(2) Date: Mar. 13, 2022

(87) PCT Pub. No.: WO2021/062250
PCT Pub. Date: Apr. 1, 2021

(65) Prior Publication Data
US 2022/0313744 A1    Oct. 6, 2022

Related U.S. Application Data

(60) Provisional application No. 62/906,070, filed on Sep. 25, 2019.

(51) Int. Cl.
*A61K 35/741* (2015.01)
*A61K 35/57* (2015.01)
(Continued)

(52) U.S. Cl.
CPC .............. *A61K 35/57* (2013.01); *A23B 5/03* (2013.01); *A23B 5/035* (2013.01); *A23C 9/154* (2013.01);
(Continued)

(58) Field of Classification Search
CPC .................................................. A61K 35/741
See application file for complete search history.

(56) References Cited

U.S. PATENT DOCUMENTS 5,817,320 A * 10/1998 Stone .................... A01N 37/18
424/278.1
6,468,525 B1    10/2002 Watson et al.
(Continued)

FOREIGN PATENT DOCUMENTS

WO    WO-2014068338 A1 *  5/2014    ........... A61K 35/744

OTHER PUBLICATIONS

Fijan, Sabina, "Microorganisms with Claimed Probiotic Properties: An Overview of Recent Literature", Int. J. Environ. Res. Public Health, vol. 11; May 5, 2014; pp. 4745-4767.
(Continued)

*Primary Examiner* — Rosanne Kosson
(74) *Attorney, Agent, or Firm* — Paradice & Li LLP

(57) ABSTRACT

Disclosed are probiotic formulations comprising fortified avian eggs and avian egg products such as egg powder, and methods for producing the same substantially no meat containing growth media such as MRS. The formulations may be used to supplement food that include, but are not limited to, baby foods, milk, and pet foods. Effective amounts of the fortified egg formulations comprising at least about $10^9$ CFU/dosage of probiotics may be used to treat health issues that include, but are not limited to, irritable bowel syndrome. The probiotic formulation may comprise bacterial strains comprising at least one of *L. casei, L. rhamnosus, B. breve, Bifidobacterium longum, L. acidophilus, L. plantarum, B. bifidum, L. fermentum, L. lactis, L. paracasei,* and *L. salivarius.*

18 Claims, 2 Drawing Sheets

Figure 1:
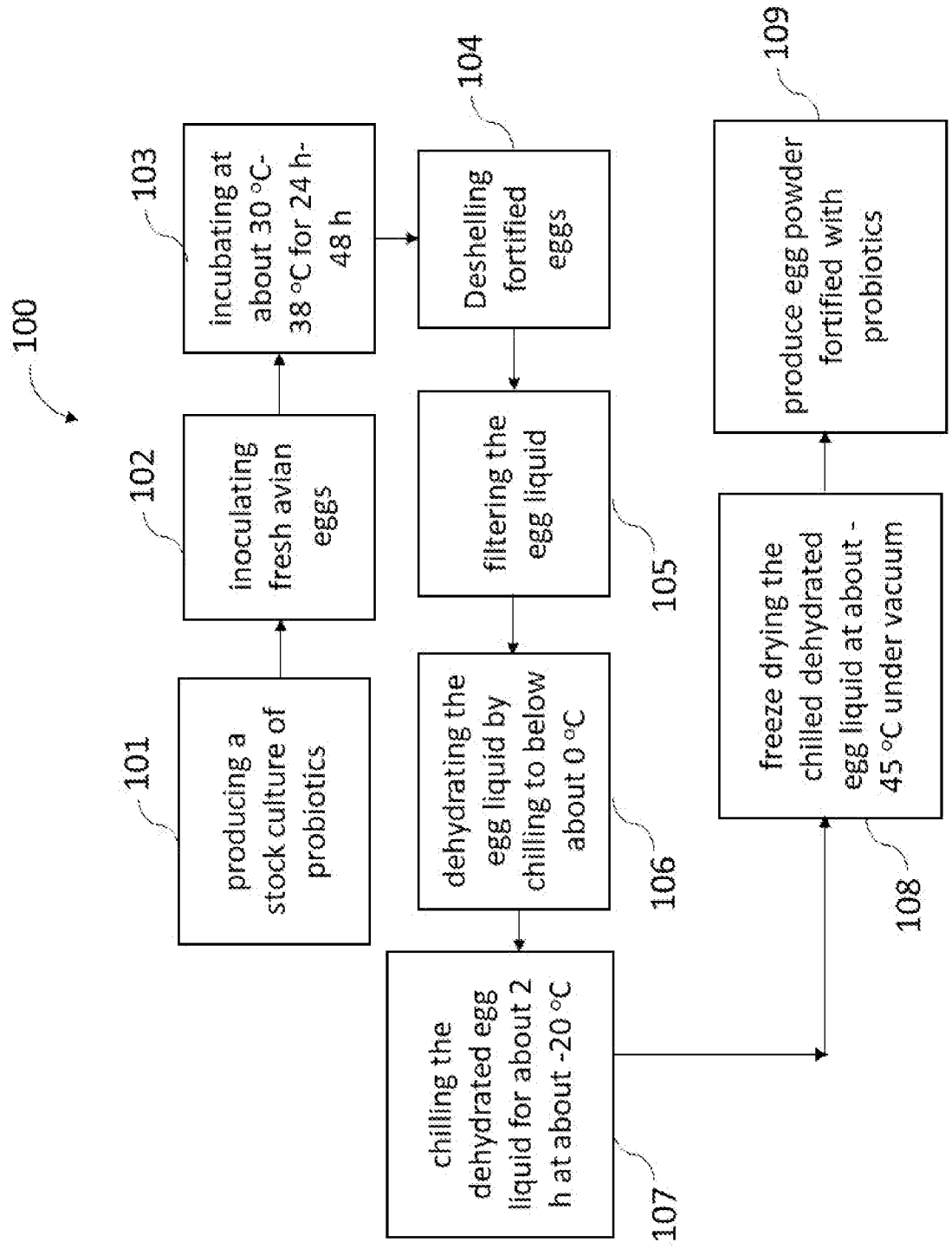

(51) Int. Cl.

| | |
|---|---|
| A23K 50/40 | (2016.01) |
| A23K 10/20 | (2016.01) |
| A23L 15/00 | (2016.01) |
| A23L 33/135 | (2016.01) |
| A23L 33/00 | (2016.01) |
| C12N 1/20 | (2006.01) |
| A23B 5/03 | (2006.01) |
| A23B 5/035 | (2006.01) |
| A23C 9/154 | (2006.01) |
| A61K 9/00 | (2006.01) |
| A61K 35/745 | (2015.01) |
| A61K 35/747 | (2015.01) |
| C12R 1/23 | (2006.01) |
| A61K 35/00 | (2006.01) |

(52) U.S. Cl.
CPC .............. *A23K 10/20* (2016.05); *A23K 50/40* (2016.05); *A23L 15/25* (2016.08); *A23L 33/135* (2016.08); *A23L 33/40* (2016.08); *A61K 9/0053* (2013.01); *A61K 35/745* (2013.01); *A61K 35/747* (2013.01); *C12N 1/20* (2013.01); *C12N 1/205* (2021.05); *A23V 2002/00* (2013.01); *A23Y 2220/03* (2013.01); *A23Y 2300/25* (2013.01); *A61K 2035/115* (2013.01); *C12R 2001/23* (2021.05)

(56) References Cited

U.S. PATENT DOCUMENTS

| | | |
|---|---|---|
| 8,697,055 B2 | 4/2014 | Farmer |
| 9,980,991 B2 | 5/2018 | Fasano et al. |
| 2014/0348796 A1 | 11/2014 | Burcelin et al. |
| 2014/0356329 A1 | 12/2014 | Leyer et al. |
| 2018/0125900 A1 | 5/2018 | Cox et al. |

OTHER PUBLICATIONS

Vlasova, A. et al., "Comparison of probiotic lactobacilli and bifidobacteria effects, immune responses and rotavirus vaccines and infection in different host species". Vet. Immunol. Immunopathol., vol. 172; Apr. 2016; pp. 72-84.

Solval, Kevin Mis et al., "Growth kinetics and lactic acid production of Lactobacillus plantarum NRRL B-4496, L. acidophilus NRRL B-4495, and L. reuteri B-14171 in media containing egg white hydrolysates", LWT-Food Science and Technology, May 2019 (Publication date), vol. 105, pp. 393-399.

Djeghri-Hocine, Baida et al., 'Evaluation of de-lipidated egg yolk and yeast autolysate as growth supplements for lactic acid bacteria culture', International Journal of Dairy Technology, Nov. 2017 (Publication date), vol. 60, No. 4, pp. 292-296.

De Oliveira, J. E. et al., 'In ovo inoculation of chicken embryos with probiotic bacteria and its effect on posthatch *Salmonella* susceptibility', Poultry Science, Apr. 1, 2014 (Publication date), vol. 93, No. 4, pp. 818-829.

Triplett, M. D. et al., 'Investigating commercial in ovo technology as a strategy for introducing probiotic bacteria to broiler embryos', Poultry Science, Feb. 1, 2018 (Publication date), vol. 97, No. 2, pp. 658-666.

Nahariah, N et al., 'Angiotensin I-converting enzyme inhibitor activity on egg albumen fermentation', Jun. 2015 (Publication date), vol. 28, No. 6, pp. 855-861.

K. Fenster, B. Freeburg, C. Hollard, C. Wong, R. R. Laursen, and A. C. Ouwehand, Microorganisms, 7, 83, 2019.

N. Nahariah, A.M. Legowo, E. Abustam, A. Hintono, Y. B. Pramono, F. N. Yuliati, Jurnal llmu dan Teknologi Peternakan (JITP), vol. 3(1), 2013.

M. Anandharaj, R. P. Rani, and M. R. Swain, "Production of High Quality Probiotics by Fermentation," Microbial Functional Foods and Nutraceuticals, ISBN: 978-1-119-04901-2, 2017.

S. E. Evivie, G-C. Huo, J.O. Igene, and X, Bian, Food and Nutrition Research, vol. 61, 1318034, 2017.

Written Opinion of ISA/KIPO for PCT/US2020/052855, dated Jan. 15, 2021.

\* cited by examiner

METHODS FOR PRODUCING PROBIOTICS FORTIFIED AVIAN EGGS AND EGG PRODUCTS AND FORMULATIONS THEREOF

RELATED APPLICATIONS

This application is a U.S. National Stage Application of International Application No. PCT/US2020/052855, filed Sep. 25, 2020, which is related to and claims the benefit of U.S. Provisional Pat. Appl. No. 62/906,070, filed Sep. 25, 2019, and titled "Methods For Producing Probiotics Fortified Avian Eggs and Egg Products and Formulations Thereof," the entire disclosure of which is hereby incorporated by reference in its entirety.

FIELD

The present invention relates to probiotic formulations comprising fortified avian eggs and avian egg products, and methods for producing the same substantially no meat containing growth media such as MRS.

BACKGROUND

Probiotics generally comprises live microorganisms like bacteria and yeasts, which when consumed in adequate amounts increase the level of microorganisms in the body (e.g., in intestines) and provides beneficial health effects. An "adequate amount" is generally considered to be a minimum dose of $10^9$ colony forming units (CFU). Probiotics may be consumed as supplements in the form of tablets. Probiotics may also be included in foods such as yogurt or added to water or other healthy drinks. Various strains of *Bifidobacterium, Lactobacillus* and *Saccharomyces* have been used as probiotics. Many probiotic supplements contain a combination of different strains in the same supplement.

Probiotic supplements have been shown to reduce irritable bowel syndrome and are viewed as an alternative to laxatives. Supplements may be in the form of capsules, tablets, powders and liquid extracts. Beneficial strains include a combination of several *Lactobacillus* and *Bifidobacterium* strains, which are typically known as lactic acid bacteria (LAB). These strains may include *B. longum, S. cerevisiae* and a combination of *L. acidophilus, L. reuteri, L. plantarum, L. rhamnosus* and *B. animalis, B. coagulans*, and *S. boulardii*. Typical dosages may be about $10^9$ CFU/day to about $20 \times 10^9$ CFU/day, while the normal dosage is about $1\text{-}10 \times 10^9$ CFU/day. Probiotics with strains that include, but are not limited to, *L. rhamnosus* GG, *L. acidophilus* and *L. bulgaricus* have been used to treat diarrhea. Probiotics may also be used to realize weight loss. For example, consumption of probiotics comprising L. gasseri, *L. rhamnosus* and *B. lactis* has been reported to reduce obesity. Other health benefits include reducing inflammation, depression and anxiety (*L. helveticus* and *B. longum*), cholesterol and cardiovascular disease (*L. reuteri* NCIMB 30242, *Enterococcus faecium*, and the combination of *L. acidophilus* La5 and *B. lactis* Bb12), and blood pressure. Probiotics are also being studied as a method of boosting the immune system. S. E. Evivie et al. (2017) provide a comprehensive report on potential applications, limitations and future perspectives of lactic acid bacteria as probiotics.

The manufacturing processes of LAB for dietary supplements and dairy applications is generally described by Fenster et al., (2019). Frozen seed stock of the desired bacterial strain may consist of a single pure strain verified to be free of contaminants and is used in sequential seed stock fermentations to achieve a desired inoculum volume. The inoculum is then transferred to a main fermentation vessel for growth. Alternatively, frozen direct vat inoculation (DVI) material, which consists of a greater count of concentrated cells, may be used to directly inoculate the main fermentation vessel. From the standpoint of bacterial stability, quality, effectiveness, and production cost, the goal is usually to limit the number of generations required to proceed from seed stock to product. The heat-treated medium used in the seed scale up and main fermentation vessel may comprise a blend of water, nitrogen sources, carbohydrates, salts, and micronutrients necessary for growth. The fermentation process is carefully controlled and after the fermentation in the main tank is completed, the cells may be concentrated by separating the cells from spent medium through centrifugation. Depending upon the final product application, stabilizer solutions for example, cryoprotectants to protect cells from injury during freezing and/or lyoprotectants to protect cells from injury during freeze-drying may be added to the cells prior to freezing. Cryoprotectants inhibit the rate of ice growth via increasing the solution viscosity and keeping the amorphous structure of ice in close proximity to the cell. Lyoprotectants stabilize the lipid bilayer structure of the cell membrane in the absence of water. Commonly used cryoprotectants and lyoprotectants are carbohydrates and peptides. In the dairy industry, skim milk powder is often used. Once the probiotic concentrate is blended with the cryoprotectant solution, various freezing processes may be utilized. One freezing technique consists of pouring cryoprotected concentrate into cans and immersing the sealed cans into a liquid nitrogen bath. The frozen cans may then be shipped for incorporating probiotics in food or beverages. Another technique consists of pelletizing the cryoprotected concentrate by dripping the concentrate into a bath of liquid nitrogen. The pellets, which are typically spheres of 4-5 mm in diameter, are then harvested and packed into bags that are stored and shipped at a temperature ranging from $-45°$ C. to $-55°$ C. Alternatively, frozen cell pellets may be used for freeze-drying (lyophilization) to a dried end-product. The frozen pellets are transferred onto trays which are capable of being temperature controlled, generally between $-40°$ C. to $+40°$ C. and are progressively heated once vacuum is established in the freeze-drying chamber. An alternative option consists of filling trays with the cryoprotected concentrate. The trays are then initially cooled down to freezing temperatures under atmospheric pressure. Once the concentrate in each tray is frozen, the shelves are gradually heated once vacuum is applied. The applied vacuum typically varies between 100 mTorr and 1000 mTorr at $-40°$ C. to $+40°$ C. Freeze-drying time varies as a function of the strain, its formulation, and the freeze-drying cycle but usually takes a few days to be completed. The advantage of freeze-drying is that the process maintains the probiotic cells at a low temperature to limit damage to the cells' structure and metabolites. After removal from the dryer, the lyophilized material is milled to a powder with a defined particle size and density. The milled material can then be used for blending with excipients (bulking agents), additional functional ingredients if required, and flow aids, depending on the needs of the customer. The blend is then used to make finished products such as capsules, sachets, or tablets. Product quality is examined periodically to make sure that the end-product is of high quality and free of contamination.

The selected raw materials including the fermentation medium may substantially impact probiotics production cost because it can affect microorganism yield and effectiveness. Further, raw material changes may be introduced by cost considerations and a change in ingredient sourcing. Changes to ingredients such as protein yeast extract, and milk protein sources are more pronounced in terms of compositional differences than in ingredients such as simple carbohydrates and salts. Depending on the nutritional requirements and sensitivities of the strains being produced, the lot-to-lot variation in complex raw ingredients may sometimes go undetected, with some strains having seemingly consistent performance, whereas the performance of other strains may be more adversely affected. With ingredients such as yeast extracts, the differences responsible for the change in strain performance may not be readily attributed to the amino acid, peptide size distribution, vitamin, nucleotide, salt, and carbohydrate levels but rather due to the presence or absence of some other unknown or less obvious components. Beet and cane molasses are used to grow baker's yeast used for the production of yeast extracts and peptones for food applications and fermentations. Carryover of components used to culture the yeast to make the yeast extracts and peptones may affect the performance of probiotic strains in a strain-dependent manner. Also, cane and beet molasses may be sourced from all over the world with performance and quality changes which can adversely impact fermentations with yeast extracts and peptones. Therefore, raw materials for the production of probiotics and dairy starter cultures need to be carefully selected and controlled. Anandharaj, M. et al. (2017) describe the selection criteria for probiotic strains and summarize new developments in fermentation technologies for producing probiotic bacteria as well as potential new approaches for enhancing the performance of these organisms during fermentation, downstream processing, and utilization in commercial products.

In addition to the growth requirements dictated by the organisms, other requirements may dictate the choice of the fermentation growth media. For example, customer preferences related to Kosher and Halal requirements but may introduce challenges because the commonly used media for culturing bacterial strains for probiotics may not comply with these requirements. Kosher requirements would require no mixing of dairy and meat products, and the use of Kosher methods. Allergen free requirement may suggest that the most common dietary allergens such as dairy, soy, gluten, and nuts must be avoided. Carbon sources derived from wheat have to be avoided because of potential contamination with gluten. For vegetarian and vegan suitable products, meat and dairy sources have to be avoided, respectively. For dietary supplements, the omission of dairy, soy, and meat extracts requires searching for alternative growth sources.

The use of eggs as a growth media for probiotics has the potential to revolutionize the production of probiotics and eliminates may restrictions related to meat and dairy based growth media. Trends in worldwide egg production, which exceeds 70 MMT, point to developing countries becoming the largest egg suppliers in the near future. Annual egg production in India, for example, is ranked just below U.S. egg production, and is reported to be about 3.8 billion kg of unprocessed, in-shell hen's eggs. The health and nutritional benefits of eggs are well known. Eggs provide a variety of vitamins and a hen's egg typically provides 77 calories, 6 grams of protein and 5 grams of healthy fat. Reports suggest that egg consumption changes the pattern of LDL particles from small, dense LDL (detrimental to health) to large LDL, which is linked to a reduced heart disease risk. Egg consumption also increases HDL, the "good" cholesterol. Further, eggs provide antioxidants such as lutein and zeaxanthin that improves eye health.

Naharaih et al. (2013) studied the growth ability of L. plantarum bacteria in egg whites and monitored total bacteria count, pH, and, total acids during different fermentation treatments as a function of three intervals, namely, 18 h, 24 h, and 30 h. 150 eggs from the same chicken farm were used. L. plantarum 0027 FNCC was isolated from milk. The results showed that fermentation time significantly increased the total bacteria count, total acid and decreased pH during the fermentation process. The difference between total bacteria count increase was significant between fermentation at 18 h ($5.884 \pm 0.157$ log CFU/g) and between both 24 h ($6.035 \pm 0.024$ log CFU/g) and 30 h ($6.131 \pm 0.095$ log CFU/g). The total acid production followed a similar trend with the acid production at 18 h ($0.077\% \pm 0.014$) being significantly lower than that measured at 24 h ($0.014\% \pm 0.167$) and the 30 h ($0.171\% \pm 0.017\%$). pH decreased during the fermentation time process and measured pH at 18 h, 24 h, and 30 h was $7.689 \pm 0.035$, and $6.434 \pm 0.501$, and $6.353 \pm 0.65$, respectively. The fermentation time of 24 h appeared to be optimum for growth of L. plantarum on egg white. Further, Naharaih et al. (2015) evaluated the potential of fermented egg albumen as a functional food that is rich in angiotensin I-converting enzyme inhibitors activity (ACE-inhibitor activity), which is antihypertensive. Six durations of fermentation (6 h, 12 h, 18 h, 24 h, 30 h, and 36 h) were examined. 600 eggs obtained from the same chicken farm were used as sources of egg albumen. Bacteria L. plantarum FNCC 0027 used in the fermentation was isolated from cow's milk. The parameters measured were the total bacteria count, dissolved protein, pH, total acid and the activity of ACE-inhibitors. The results showed that fermentation time had a significant effect on the measured parameters. Total bacteria increased significantly during fermentation for 6 h, 12 h, 18 h, and 24 h from about 6 $\log_{10}$ CFU ($10^6$) to about 9 $\log_{10}$ CFU ($10^9$) and then decreased with the increasing time of fermentation to 30 h and 36 h. The pH value decreased markedly during fermentation from about 7.3 pH to about 6.3 pH. The egg albumen which was fermented for 18 h resulted in a functional food that was rich in ACE-inhibitor activity. K. M. Solval et al. (2019) studied the performance of fermentation media containing egg white hydrolysates (EWH) and/or dried egg white (DEW) with standard MRS media on the growth of lactic acid bacteria (LAB) Lactobacillus plantarum NRRL B-4496, L. acidophilus NRRL B-4495, and L. reuteri B-14171. Four fermentation media for growing LAB were evaluated: (1) standard MRS media, (2) MRS with no nitrogen source (MRSN), (3) MRSN with EWH (MRSN-EWH), and (4) MRSN with DEW (MRSN-DEW). The fermentation media were incubated with LAB at 37° C. for 24 h and periodically sampled to obtain growth curves, pH, and titratable acidity. The results showed that EWH had higher amounts of free amino acids compared to DEW. Threonine and leucine were the predominant free amino acids found in EWH. MRSN-EWH was better at promoting the growth of L. acidophilus NRRL B-449 and L. reuteri B-14171 in terms biomass production, maximum growth rate and titratable acidity than MRS. MRS and MRSN-EWH media supported greater cell biomass yields than MRSN and MRSN-DEW for L. plantarum NRRL B-4496. This study showed that egg white hydrolysates can be used as fermentation media to enhance the growth of probiotic lactic acid bacteria.

Probiotic formulations comprising fortified avian eggs and avian egg products, and methods for producing the same with substantially no meat containing growth media such as MRS are needed.

BRIEF DISCLOSURE

Disclosed is an exemplary method of producing avian eggs fortified with probiotics comprising producing a stock culture of probiotics in water using a predetermined probiotic formulation at between about 20° C. and about 37° C., inoculating fresh avian eggs with the stock culture, and incubating the inoculated eggs at a predetermined incubation temperature for a predetermined incubation period wherein the CFU count of the probiotics in the inoculated eggs is at least about $10^5$/ml. The predetermined incubation temperature may be between about 30° C. and about 38° C. The predetermined incubation temperature may be about 37° C. The predetermined incubation period may be between about 24 h and about 48 h. The predetermined probiotic formulation may comprise bacterial strains comprising at least one of *L. casei, L. rhamnosus, B. breve, Bifidobacterium longum, L. acidophilus, L. plantarum, B. bifidum, L. fermentum, L. lactis, L. paracasei*, and *L. salivarius*. The CFU of each bacterial strain in the probiotic formulation may be between about $0.12 \times 10^9$ and about $3 \times 10^9$. The CFU count of the probiotics in the inoculated eggs may between about $10^9$ and about $10^{10}$ CFU/ml. The predetermined probiotic formulation may comprise probiotic supplements having a total CFU value of at least $10^{10}$ CFU/dosage. The fresh avian eggs may comprise hen eggs. The fresh avian eggs may comprise ostrich eggs. The fresh avian eggs may comprise whole shell eggs. The exemplary method may further comprise the step of boiling the fortified avian eggs to produce hard-boiled fortified avian eggs. The fresh avian eggs may comprise egg liquid contained within the shell of each egg. The exemplary method may further comprising the steps of deshelling the fortified eggs, filtering the egg liquid to remove shell pieces, dehydrating the egg liquid by chilling to below about 0° C., chilling the dehydrated egg liquid for about 2 h at about −20° C. and, freeze drying the chilled dehydrated egg liquid at about −45° C. under vacuum to produce egg powder fortified with probiotics. The egg liquid may be pasteurized prior to the dehydrating step. Pasteurization may be done by heating the egg liquid at between about 60° C. and about 65° C. for at most 5 min. Egg powder may also be produced using an exemplary method comprising deshelling the fortified eggs and filtering the egg liquid to remove shell pieces, pasteurizing the egg liquid, and spray drying droplets of the pasteurized egg liquid using air at temperatures between about 80° C. and about 200° C. to produce egg powder fortified with probiotics. The egg yolks may be separated from the egg liquid of the avian eggs fortified with probiotics and using the egg white liquid to produce egg white powder fortified with probiotics.

Disclosed is an exemplary method of producing avian eggs fortified with probiotics, comprising producing a stock culture of probiotics in MRS growth media with Accession number ATCC #416 at about 37° C. using a predetermined probiotic composition, inoculating fresh avian eggs with the stock culture, and incubating the inoculated eggs at about 37° C. for between about 24 h and about 96 h, wherein the CFU count of the probiotics in the inoculated eggs is at least $10^5$/ml. The probiotic composition may comprise at least one of *L. acidophilus* with Accession No. ATCC #BAA2832 and *B. bifidium* with Accession No. ATCC #BAA2850. Egg powder fortified with probiotics may be produced by processing the avian eggs fortified with probiotics as disclosed herein.

Disclosed is an egg powder formulation fortified with probiotics which may be produced by inoculating fresh avian eggs with a stock culture of probiotics in water using a predetermined probiotic formulation at between about 20° C. and about 37° C. the stock culture, incubating the inoculated eggs at a predetermined incubation temperature for a predetermined incubation period, and freeze drying the egg liquid collected after the incubation step wherein the CFU count of the probiotics in the fortified egg powder is at least about $10^5$/ml. The fresh avian eggs may comprise whole shell eggs. The fresh avian eggs may comprise egg liquid contained within the shell of each egg. The predetermined probiotic formulation may comprise bacterial strains comprising at least one of *L. casei, L. rhamnosus, B. breve, Bifidobacterium longum, L. acidophilus, L. plantarum, B. bifidum, L. fermentum, L. lactis, L. paracasei*, and *L. salivarius*. The CFU of each bacterial strain in the probiotic formulation may be between about $0.12 \times 10^9$ and about $3 \times 10^9$. The predetermined incubation temperature may be between about 30° C. and about 38° C. The predetermined incubation period may be between about 16 h and about 72 h.

Disclosed is an exemplary baby food formulation comprising egg powder fortified with probiotics produced using one of the exemplary methods disclosed herein.

Disclosed is an exemplary milk formulation comprising egg powder fortified with probiotics produced using one of the exemplary methods disclosed herein.

Disclosed is an exemplary pet foods formulation comprising egg powder fortified with probiotics produced using one of the exemplary methods disclosed herein.

Disclosed is an exemplary method of treating irritable bowel syndrome comprising administering an effective amount of the fortified egg powder wherein the CFU count may be between about $10^9$ and about $10^{10}$ CFU/dosage administered at a frequency of at least once a day.

Disclosed is an exemplary method of producing avian egg products fortified with probiotics, the method comprising producing a stock culture of probiotics in water using a predetermined probiotic composition at between about 20° C. and about 37° C., inoculating fresh avian eggs with the stock culture, incubating the inoculated eggs at between about 30° C. and 38° C. for between about 16 h and about 72 h, cooking the eggs fortified with probiotics, and freeze drying the cooked eggs, wherein the CFU of the probiotics in the inoculated eggs is at least about $10^5$/ml. The fresh avian eggs may comprise whole shell eggs.

Other features and advantages of the present disclosure will be set forth, in part, in the descriptions which follow and the accompanying drawings, wherein the preferred aspects of the present disclosure are described and shown, and in part, will become apparent to those skilled in the art upon examination of the following detailed description taken in conjunction with the accompanying drawings or may be learned by practice of the present disclosure. The advantages of the present disclosure may be realized and attained by means of the instrumentalities and combinations particularly pointed out in the appendant claims.

DRAWINGS

The foregoing aspects and many of the attendant advantages of this disclosure will become more readily appreciated as the same becomes better understood by reference to the following detailed description, when taken in conjunction with the accompanying drawing, wherein:

FIG. 1. Schematic diagram of an exemplary method for producing probiotics fortified avian egg powder.

Figure 2:
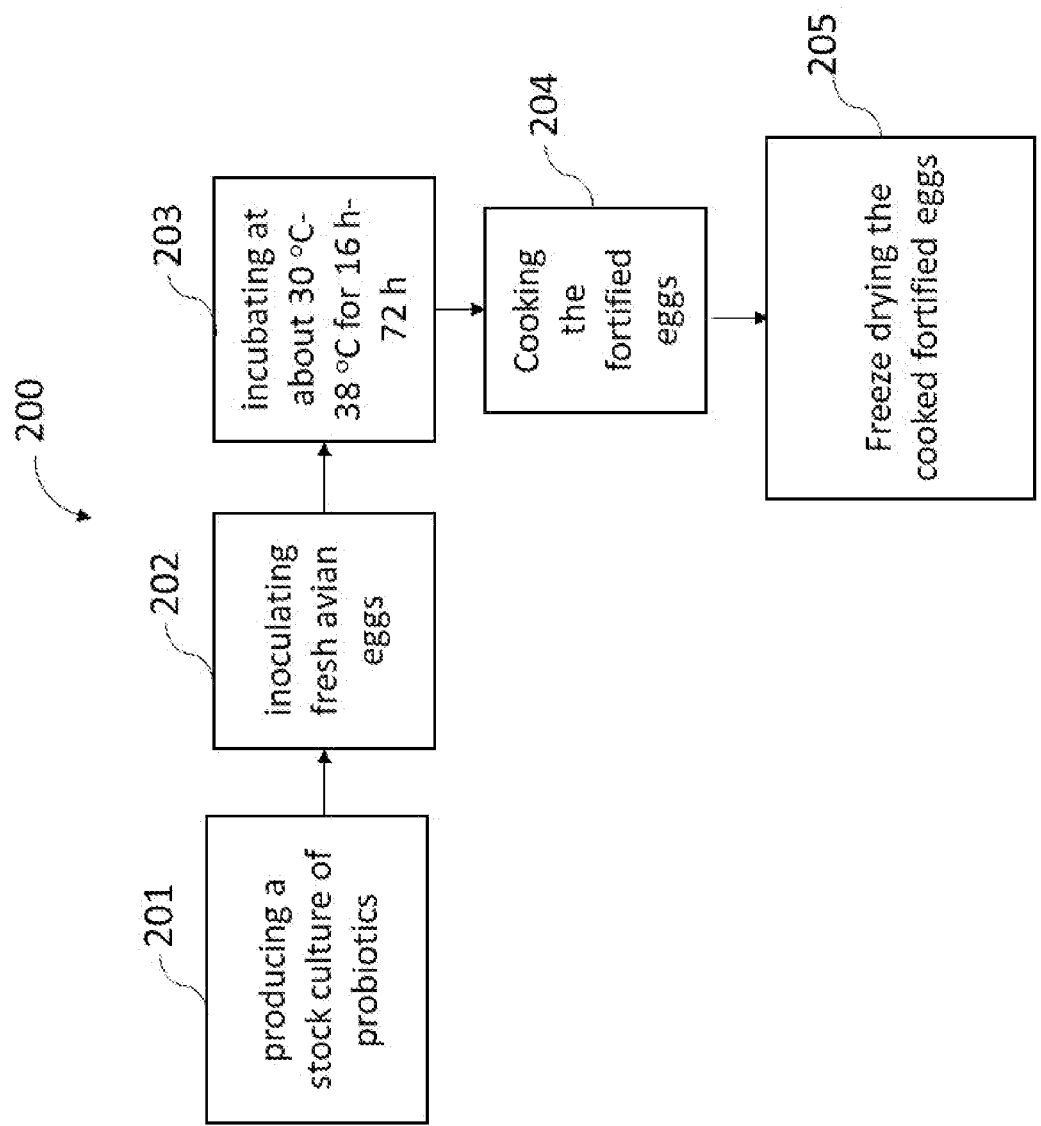

FIG. 2. Schematic diagram of exemplary method for producing probiotics fortified avian egg products.

All reference numerals, designators and callouts in the figure is hereby incorporated by this reference as if fully set forth herein. The failure to number an element in a figure is not intended to waive any rights. Unnumbered references may also be identified by alpha characters in the figures and appendices.

The following detailed description includes references to the accompanying drawings, which form a part of the detailed description. The drawing shows, by way of illustration, specific embodiments in which the pilot assembly and methods may be practiced. These embodiments, which are to be understood as "examples" or "options," are described in enough detail to enable those skilled in the art to practice the present invention. The embodiments may be combined, other embodiments may be utilized or structural or logical changes may be made without departing from the scope of the invention. The following detailed description is, therefore, not to be taken in a limiting sense and the scope of the invention is defined by the appended claims and their legal equivalents.

In this document, the terms "a" or "an" are used to include one or more than one, and the term "or" is used to refer to a nonexclusive "or" unless otherwise indicated. In addition, it is to be understood that the phraseology or terminology employed herein, and not otherwise defined, is for the purpose of description only and not of limitation. For construing the scope of the term "about," the error bounds associated with the values (dimensions, operating conditions etc.) disclosed is ±10% of the values indicated in this disclosure. Unless otherwise specified, the word "substantially" used before a specific word includes the meanings "considerable in extent to that which is specified," and "largely but not wholly that which is specified." In addition, "sound" and "noise" may be interchangeably used.

DETAILED DISCLOSURE

Particular aspects of the invention are described below in considerable detail for the purpose for illustrating its principles and operation. However, various modifications may be made, and the scope of the invention is not limited to the exemplary aspects described.

Disclosed in an exemplary method for producing probiotics using ostrich egg as the growth medium. Eggs from North African ostriches (*Struthio camelus camelus*) were used for this purpose. Each egg weighed about 70-80 oz. Stock cultures of *L. acidophilus* (LA) from American Type Culture Collection (Rockville, Md.) with Accession No. ATCC #BAA2832 and *B. bifidium* (Bb) with Accession No. ATCC #BAA2850 were grown in de Man, Rogosa, and Sharpe (MRS) medium, ATCC #416, under low oxygen condition at 37° C. The MRS medium was selected to favor growth of the above bacterial strains. The LA and Bb cultures were then inoculated into whole shell ostrich eggs and incubated at 37° C. for 4 days. LA and Bb were extracted and the total bacterial count in each culture was measured. The total bacterial count for both LA and Bb was found to be about $10^5$ CFU/ml.

In another exemplary method 100 (FIG. 1), fortified eggs and egg products were produced by injecting stock culture, produced in step 101, comprising a mixture comprising *L. casei* (about $3\times10^9$ CFU), *L. rhamnosus* (about $2.6\times10^9$ CFU), *B. breve* (about $1.2\times10^9$ CFU), *Bifidobacterium longum* (about $1.2\times10^9$ CFU), *L. acidophilus* ($1.2\times10^9$ CFU), *L. plantarum* ($1.2\times10^9$ CFU), *B. bifidum* ($0.6\times10^9$ CFU), *L. fermentum* (0.60 billion), *L. lactis* ($0.12\times10^9$ CFU), *L. paracasei* ($0.12\times10^9$ CFU), *L. salivarius* ($0.12\times10^9$ CFU) into fresh, large, grade A hen eggs. The stock culture was prepared by dissolving one capsule of a commercially available probiotic supplement Super Probiotic Blend, supplied by Pharmaca Inc. (Boulder, Colo.) in about 2 ml of filtered water at ambient temperature. Between about 0.5 ml and about 1 ml of the culture was then injected into the egg white of whole shell eggs in step 102. The eggs were then incubated for between about 24 h and about 48 h at between about 30° C. and 38° C. in step 103, and at preferably about 37° C. and cooled to obtain eggs fortified with probiotics. The probiotic supplements comprised a Maltodextrin, vegetarian capsule (modified cellulose purified water), inulin, magnesium stearate (vegetable grade), silicon dioxide, and ascorbic acid. The supplements do not contain any artificial preservatives color, sweeteners, gluten, or yeast. Other compositions of probiotics (bacterial strains or combination thereof) may also be used to inoculate fresh hen eggs. The fortified eggs are also free of any meat products typically found in MRS growth media and meets Halal and Kosher requirements.

In another exemplary method for providing fortified eggs to consumers with increased shelf life, the fortified eggs obtained using the exemplary methods described above may be boiled to yield hard-boiled eggs, fortified by probiotics. Fortified eggs may be poached and fried as well.

In exemplary method 100, fortified eggs obtained in step 103 may be processed to yield egg powder. Fortified eggs may be broken and deshelled in step 104 and filtered to remove egg-shell pieces in step 105. The egg liquid may then be pumped into a storage vessel or silo and stored at low temperature. In step 106, the egg liquid may be dehydrated wherein the egg liquid is converted to crystallized form at below about 0° C. and water/moisture is removed by sublimation. In step 107, the dehydrated liquid is then chilled at about −20° C. for about 2 h and freeze dried at about −45° C. under vacuum in step 108 to produce fortified egg powder in step 109. After the filtration step, the egg liquid may be pasteurized by treating at about 60-65° C. for less than about 5 min. if the probiotics are not subject to denaturation of the proteins in the bacterial strains. Egg liquid may also be dried by conventional spray process wherein the egg liquid droplets are dehydrated by a hot air stream that is maintained at a temperature of between about 80° C. and about 200° C. The spray process may denature some bacterial strains at elevated temperature dehydration and is not preferred unless bacterial strains are heat resistant or are in the form of spores that are resistant to heat. Spores may be subsequently activated to vegetative cells. Spores are generally resistant to heat, dessication, chemicals, and radiation. Bacteria can form endospores in approximately 6 to 8 h after being exposed to adverse conditions. The normally growing cell that forms the endospore is called a vegetative cell. Spores are metabolically inactive and dehydrated.

In another exemplary method, fortified avian eggs obtained in step 103 may be scrambled, for example, with extra virgin oil and consumed. The scrambled eggs may also be dehydrated for about 8 h and powdered to produce fortified avian egg powder.

In another exemplary method, fortified egg powder may be produced by blending egg powder produced using either spray drying or freeze drying with a suitable probiotic composition including the compositions previously described. The probiotic composition is preferably in at least one of liquid or solid form.

In another exemplary method for producing fortified egg powder using any one of the methods described previously, the egg white may be separated from the yoke prior to the filtration step to produce fortified egg white powder.

The exemplary fortified eggs either in fresh or processed form as described above may be used as a supplement in baby foods (e.g., Gerber baby foods, milk powder, and the like), and in any number of drinks that include, but are not limited to, juice, tea, milk, and coffee. Fortified egg powder may be flavored and added to drinking water also. The exemplary fortified egg products may also be used as supplements in pet foods, skin and body care products.

Disclosed is an exemplary method 200 for producing eggs and products fortified with probiotics comprises the steps of producing a stock culture of probiotics in water using a predetermined probiotic composition at between about 20° C. and about 37° C. in step 201, inoculating raw (fresh) avian eggs with the stock culture in step 202, incubating the inoculated eggs between about 30° C. and 38° C. during an incubation period between about 16 h and about 72 h, in step 203, cooking the eggs in step 204 and freeze drying the cooked eggs in step 205. Water may be distilled water or purified water produced using suitable methods. The incubation temperature may be about 37° C. The incubation period may be between about 16 h and about 48 h. The incubation period may be between about 4 h and about 36 h. Eggs may be cooked using at least one of sous vide (under vacuum) cooking, using an air fryer, boiled, and poached. A cooking method is selected to ensure that the freeze-fried cooked egg products may comprise probiotics counts (CFU/ml) of between about $10^9$ and about $10^{10}$. The egg white may be separated from the yoke prior to cooking to produce egg white products fortified with probiotics. During sous vide cooking, the eggs may vacuum sealed, for example, in a bag and then cooked in a water bath held at about 120° F. The cooking time may be between 10 min and 20 min. An air fryer circulates hot air and food is cooked by convection heating. Cooking eggs fortified with probiotics in air fryer may be accomplished at about 120° F. using a cooking time of between about 15 min and 20 min. The freeze-dried cooked egg products may be rehydrated by adding water prior to consumption. The exemplary fortified eggs either in fresh or processed form as described above may be used as a supplement in baby foods (e.g., Gerber baby foods, milk powder, and the like), mayonnaise, and in any number of drinks that include, but are not limited to, juice, tea, milk, and coffee. Fortified egg powder may be flavored and added to drinking water also. The exemplary fortified egg products may also be used as supplements in pet foods, skin and body care products.

The probiotic fortified products produced from exemplary methods 100 and 200 may be used to treat irritable bowel syndrome using a treatment method comprising administering an effective amount of the fortified egg powder wherein the CFU count may be between about $10^9$ and about $10^{10}$ CFU/dosage administered at a frequency of at least once a day. The effective amount of the fortified egg powder wherein the CFU count may be at least about $10^9$ CFU/dosage administered at a frequency of at least once a day.

The Abstract is provided to comply with 37 C.F.R. § 1.72(b), to allow the reader to determine quickly from a cursory inspection the nature and gist of the technical disclosure. It should not be used to interpret or limit the scope or meaning of the claims.

Although the present disclosure has been described in connection with the preferred form of practicing it, those of ordinary skill in the art will understand that many modifications can be made thereto without departing from the spirit of the present disclosure. Accordingly, it is not intended that the scope of the disclosure in any way be limited by the above description.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure both independently and as an overall system and in both method and apparatus modes.

Further, each of the various elements of the disclosure and claims may also be achieved in a variety of manners. This disclosure should be understood to encompass each such variation, be it a variation of an implementation of any apparatus implementation, a method or process implementation, or even merely a variation of any element of these.

Particularly, it should be understood that the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this disclosure is entitled. It should be understood that all actions may be expressed as a means for taking that action or as an element which causes that action. Similarly, each physical element disclosed should be understood to encompass a disclosure of the action which that physical element facilitates.

In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Further, the use of the transitional phrase "comprising" is used to maintain the "open-end" claims herein, according to traditional claim interpretation. Thus, unless the context requires otherwise, it should be understood that variations such as "comprises" or "comprising," are intended to imply the inclusion of a stated element or step or group of elements or steps, but not the exclusion of any other element or step or group of elements or steps. Such terms should be interpreted in their most expansive forms so as to afford the applicant the broadest coverage legally permissible.

REFERENCES

1. M. Anandharaj, R. P. Rani, and M. R. Swain, "Production of High-Quality Probiotics by Fermentation," Microbial Functional Foods and Nutraceuticals, ISBN: 978-1-119-04901-2, 2017.
2. S. E. Evivie, G-C. Huo, J. O. Igene, and X, Bian, *Food and Nutrition Research*, vol. 61, 1318034, 2017.
3. K. Fenster, B. Freeburg, C. Hollard, C. Wong, R. R. Laursen, and A. C. Ouwehand, *Microorganisms*, 7, 83, 2019.

4. N. Nahariah, A. M. Legowo, E. Abustam, A. Hintono, Y. B. Pramono, F. N. Yuliati, *Jurnal Ilmu dan Teknologi Peternakan (JITP)*, Vol. 3(1), 2013.
5. N. Nahariah, A. M. Legowo, E. Abustam, and A. Hintono, *Asian Australas. J. Anim. Sci.*, Vol. 28 (6), 855-861, June 2015.
6. K. M. Solval, A. Chouljenko, A. Chotiko, S. Sathivel, *LWT-Food Science and Technology*, 105, 393-399, 2019.

What is claimed is:

1. A method of producing avian eggs fortified with probiotics, the method comprising:
    producing a stock culture of probiotics in water using a predetermined probiotic formulation at between about 20° C. and about 37° C.;
    inoculating fresh avian eggs with the stock culture; and,
    incubating the inoculated eggs at a predetermined incubation temperature for a predetermined incubation period wherein the CFU count of the probiotics in the inoculated eggs is at least about $10^5$/ml.

2. The method of claim 1 wherein the predetermined incubation temperature is between about 30° C. and about 38° C.

3. The method of claim 1 wherein the predetermined incubation temperature is about 37° C.

4. The method of claim 1 wherein the predetermined incubation period is between about 24 h and about 48 h.

5. The method of claim 1 wherein the predetermined probiotic formulation comprises *L. acidophilus*.

6. The method of claim 5 wherein the CFU of *L. acidophilus* in the probiotic formulation is between about $0.12 \times 10^9$ and about $3 \times 10^9$.

7. The method of claim 1 wherein the CFU count of the probiotics in the inoculated eggs is between about $10^9$ and about $10^{10}$ CFU/ml.

8. The method of claim 1 wherein the predetermined probiotic formulation comprises probiotic supplements having a total CFU value of at least $10^{10}$ CFU/dosage.

9. The method of claim 1 wherein the fresh avian eggs comprise hen eggs.

10. The method of claim 1 wherein the fresh avian eggs comprise ostrich eggs.

11. The method of claim 1 further comprising the step of boiling the fortified avian eggs to produce hard-boiled fortified avian eggs.

12. The method of claim 1 wherein the fresh avian eggs comprise whole shell eggs.

13. The method of claim 1 wherein the fresh avian eggs comprise egg liquid contained within the shell of each egg.

14. The method of claim 12 further comprising the steps of:
    deshelling the fortified eggs;
    filtering the egg liquid to remove shell pieces;
    dehydrating the egg liquid by chilling to below about 0° C.;
    chilling the dehydrated egg liquid for about 2 h at about −20° C.; and,
    freeze drying the chilled dehydrated egg liquid at about −45° C. under vacuum to produce egg powder fortified with probiotics.

15. The method of claim 14 wherein the egg liquid is pasteurized prior to the dehydrating step.

16. The method of claim 15 wherein pasteurization is done by heating the egg liquid at between about 60° C. and about 65° C. for at most 5 min.

17. The method of claim 13 further comprising the step of freeze drying the egg liquid after the incubation step.

18. The method of claim 1 wherein the predetermined incubation period is between about 4 h and about 72 h.

\* \* \* \* \*